(12) United States Patent
Dorn et al.

(10) Patent No.: US 8,657,867 B2
(45) Date of Patent: Feb. 25, 2014

(54) STENT DELIVERY DEVICE

(75) Inventors: Jürgen Dorn, Neulussheim (DE);
Martina Hoffman, Stutensee (DE);
Daniel Dietrich, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 287 days.

(21) Appl. No.: 13/142,823

(22) PCT Filed: Oct. 29, 2009

(86) PCT No.: PCT/EP2009/064273
§ 371 (c)(1),
(2), (4) Date: Aug. 19, 2011

(87) PCT Pub. No.: WO2010/076057
PCT Pub. Date: Jul. 8, 2010

(65) Prior Publication Data
US 2011/0301689 A1 Dec. 8, 2011

Related U.S. Application Data

(60) Provisional application No. 61/141,411, filed on Dec. 30, 2008.

(30) Foreign Application Priority Data

Dec. 30, 2008 (GB) ...................... 0823658

(51) Int. Cl.
*A61F 2/06* (2013.01)
(52) U.S. Cl.
USPC ...................................... 623/1.11
(58) Field of Classification Search
USPC ........ 606/108, 151, 198; 623/1.11, 1.12, 1.23
See application file for complete search history.

(56) References Cited

U.S. PATENT DOCUMENTS 5,246,452 A  9/1993  Sinnott
6,254,628 B1 *  7/2001  Wallace et al. .............. 623/1.12
(Continued)

FOREIGN PATENT DOCUMENTS

EP  0732087 B1  6/2003
WO  9953865 A1  10/1999
(Continued)

OTHER PUBLICATIONS

GB 0823658.8 Search Report dated Apr. 8, 2009.
(Continued)

*Primary Examiner* — Victor Nguyen
(74) *Attorney, Agent, or Firm* — Rutan & Tucker, LLP

(57) ABSTRACT

A delivery device is provided for delivering a stent device. The stent device (2) is radially expandable from a radially reduced, delivery configuration to a radially expanded, deployment configuration. A restraining sheath (4) is mounted coaxially over the stent device for maintaining the stent device in the delivery configuration. The restraining sheath has a line of weakness (6) extending axially thereal-ong. A pull member is provided, which is to be pulled so as to split the restraining sheath at the line of weakness and withdraw the restraining sheath from over the stent device. The pull member and the line of weakness are located on opposing sides of the restraining sheath. The pull member (5) is wrapped around a distal end of the restraining sheath. The wrap around portion may be formed by a hook of a metal pull member. The wrap around portion may be formed by an open loop of polymer thread. Both ends of the open loop may extend proximally from the restraining sheath and the stent device with one of the ends being fixed to the delivery device and the other being moveable to provide a pull end.

17 Claims, 4 Drawing Sheets

(56) References Cited

U.S. PATENT DOCUMENTS

| | | | |
|---|---|---|---|
| 6,383,171 | B1 | 5/2002 | Gifford et al. |
| 6,645,238 | B2 * | 11/2003 | Smith .................. 623/1.11 |
| 2006/0015171 | A1 | 1/2006 | Armstrong |
| 2008/0243224 | A1 | 10/2008 | Wallace et al. |

FOREIGN PATENT DOCUMENTS

| | | | |
|---|---|---|---|
| WO | 2004096091 | A8 | 3/2005 |
| WO | 2006032686 | A1 | 3/2006 |
| WO | 2007027284 | A1 | 3/2007 |
| WO | 2009050265 | A1 | 4/2009 |
| WO | 2009135934 | A1 | 11/2009 |
| WO | 2010076057 | A1 | 7/2010 |

OTHER PUBLICATIONS

PCT/EP2009/064273 filed Oct. 29, 2009 International Preliminary Report on Patentability dated Jul. 5, 2011 and Written Opinion dated Dec. 28, 2009.

PCT/EP2009/064273 filed Oct. 29, 2009 International Search Report dated Dec. 28, 2009.

* cited by examiner

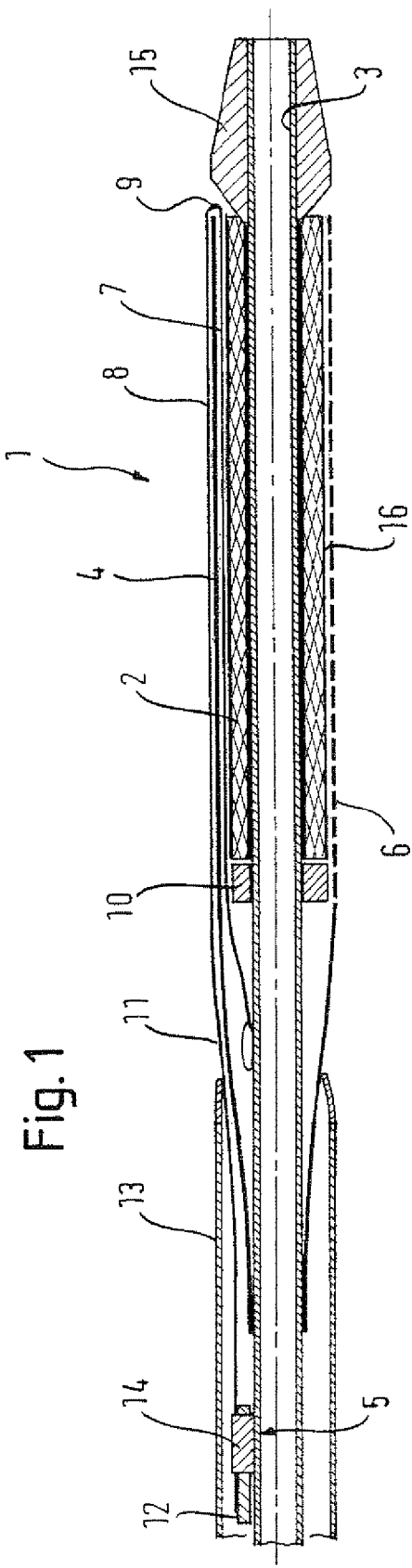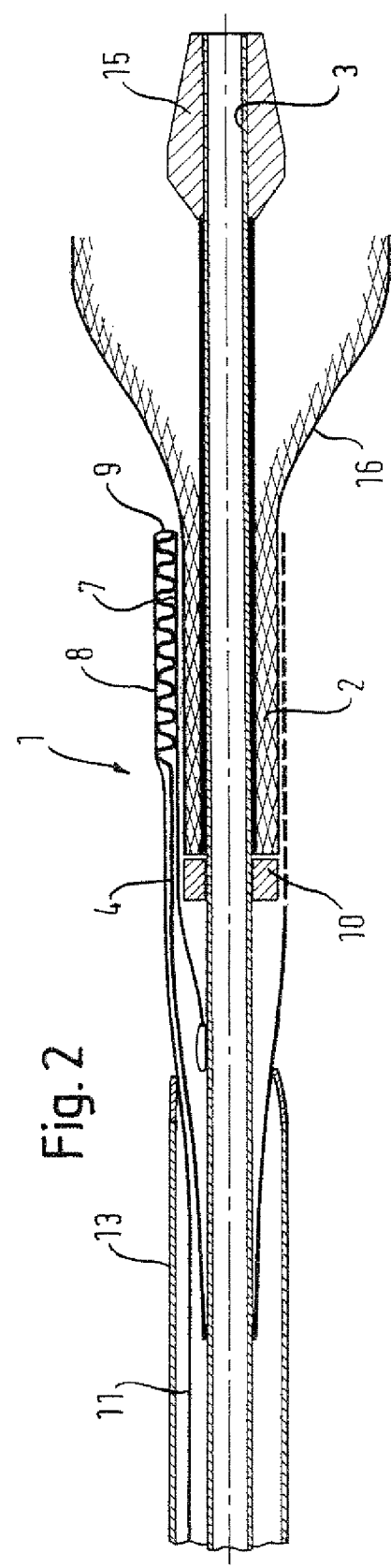

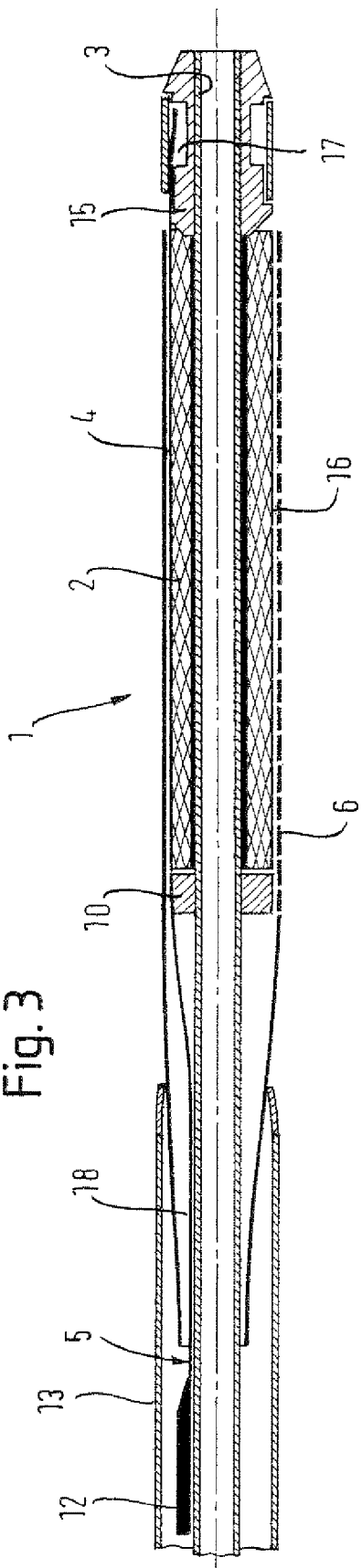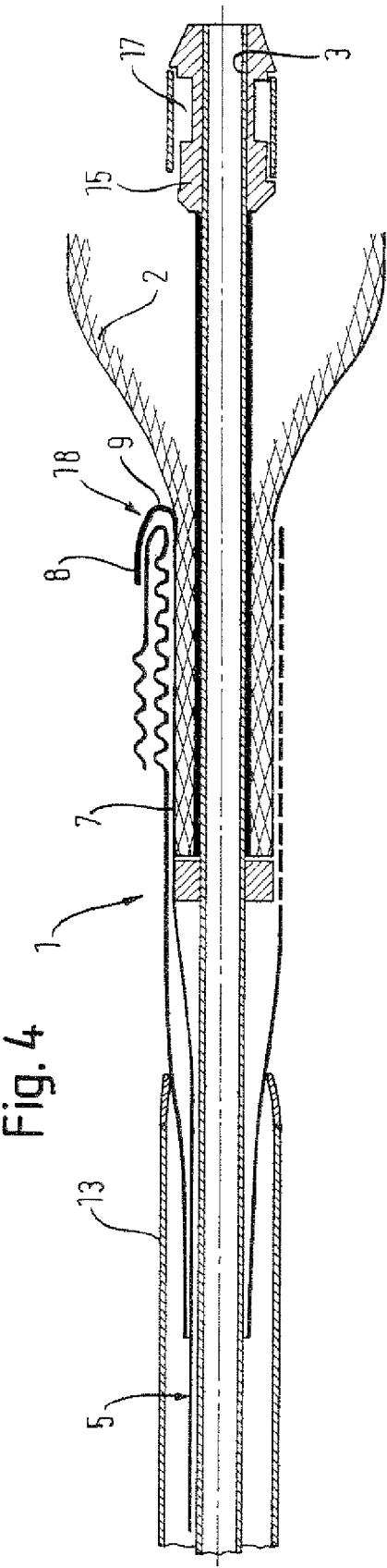

STENT DELIVERY DEVICE

PRIORITY

This application is a U.S. national stage application under 35 USC §371 of International Application No. PCT/EP2009/064273, filed Oct. 29, 2009, claiming priority to United Kingdom Patent Application No. 0823658.0, filed Dec. 30, 2008, and to U.S. Provisional Application No. 61/141,411, filed Dec. 30, 2008, each of which is incorporated by reference in its entirety into this application.

FIELD OF THE INVENTION

The present invention is concerned with a delivery device for releasing a stent device from a restraining sheath in order to deliver the stent device to a treatment site within a patient. The stent device is radially contained within the restraining sheath in a radially reduced, delivery configuration. The restraining sheath has to be released in order that the stent device can be radially expanded into a deployed configuration for holding open a bodily lumen.

BACKGROUND OF THE INVENTION

Stent devices are used in the treatment of diseased human or animal bodily lumens to provide structural support to the lumens. Of particular relevance to the present invention are stent devices for supporting and holding open vasculature lumens of the human body.

In order for the stent devices to reach the treatment site, a delivery device is used that passes through vascular passageways, often traversing relatively long and tortuous paths. Surgical procedures for delivering stent devices to various locations in the body are known to one skilled in the art. Thin and flexible delivery devices are advantageous for reaching challenging treatment sites.

With the objective of a reduced profile delivery device, a stent device is generally provided in a radially reduced delivery state. The stent device may be crimped onto an inner support member and a restraining sheath is disposed over the stent device to maintain the stent device in the radially reduced configuration. The delivery device will then be fed through relevant passages of the vasculature with the stent device maintained in the delivery configuration by the restraining sheath. Once at the treatment site, the restraining sheath is operated upon so that the stent device can radially expand to a deployed configuration for supporting and holding open a portion of a vein or artery or other bodily lumen.

Stent devices have a structural framework for supporting a diseased vasculature. Different arrangements for the structural framework are found throughout the relevant art. Often, the stent device will be formed from a seamless tubular workpiece into an elongate device having a number of axially spaced rings of stent material with each ring formed of zig-zagging struts and with each ring connected to another by several circumferentially distributed connector struts. The inner major surface, the outer major surface or both may be covered to make the stent device liquid impermeable, which is then often named a stent graft. The framework may, however, be uncovered, which is then often named a bare stent.

Stent devices may be balloon expandable or they may be self-expandable. Balloon expandable stents may be radially expanded into the deployed configuration by action of a circumferential balloon disposed between the inner member and the stent device. The balloon is inflated, usually by injection of saline solution, thereby expanding the stent device into the deployed configuration. The present applicant has particular experience with self-expandable stent devices. These can be made of shape memory materials, such as the shape memory Nickel Titanium alloy known as Nitinol. Nitinol can be constructed into a desired deployed configuration and then crimped into the reduced profile delivery configuration. As long as the Nitinol stent device is kept below a solid phase transition temperature, the deformation of the reduced profile delivery configuration will be kept. Once raised above the phase transition temperature, such as at a body temperature, the Nitinol stent device will return to its original, radially expanded delivery configuration when it is allowed to do so, that is when it is released by the restraining sheath.

The prior art is replete with examples of ways to release the stent device from the overlaying restraining sheath. Two examples are prevalent.

One example is to slide the restraining sheath over the stent device in order to expose the stent device. The frictional forces between the stent device and the restraining sheath can be great, particularly as the stent device becomes more highly crimped, which causes increased radial forces straining on the sheath as it slides over the stent device. Similarly, a longer stent device will have greater frictional contact with the restraining sheath. This latter contributor to the frictional forces between the restraining sheath and the stent device is important in applications where stent devices have lengths greater than 200 mm and up to 300 mm or more. A pull member, extending proximally to a handle of the delivery device, is generally used to retract the outer sheath by pulling on it to move the outer sheath relative to the stent device to expose the stent device. One example of this form of release of the stent device can be found from WO 2004/096091. The high frictional forces involved in dragging the restraining sheath over the stent device can be damaging to the stent device and can make the pull force required to move the restraining sheath undesirably high.

Another example of a general way to release a stent device is to tear the restraining sheath axially along the stent device, thereby releasing the stent device to radially expand. One or more perforation lines can be provided in combination with a pull member running adjacent the perforation line or lines. As the pull member is pulled, the restraining sheath is torn at the perforation line to radially release the stent device. We found U.S. Pat. No. 5,246,452, US 2008/0243224 and WO 99/53865 to be interesting example disclosures of such technology. Also known is the tearing of the restraining sheath by using a pull member to cut therethrough, such as with a wire pull member that is able to slice through the restraining sheath. An interesting example of this kind of technology is disclosed in EP 0732087. One difficulty with such release mechanisms is that all or a part of the restraining sheath remains between the stent device and a wall of the bodily lumen. This may not be desirable in terms of properly engaging the stent device with the wall of the bodily lumen and may be disadvantageous in so far as it only allows certain materials to be used for the restraining sheath, which are long-term biocompatible.

Accordingly, it is an objective of the present invention to provide a mechanism for releasing a stent device from a restraining sheath that removes the restraining sheath from between the stent device and a wall of the vascular lumen and also allows a relatively low pulling force in carrying out the stent device release.

SUMMARY OF THE INVENTION

The present invention provides a stent delivery device, comprising:

a stent device, which is radially expandable from a radially reduced, delivery configuration to a radially expanded, deployment configuration;

a restraining sheath mounted coaxially over the stent device for maintaining the stent device in the delivery configuration;

the restraining sheath having a line of weakness extending axially therealong;

a pull member to be pulled so as to split the restraining sheath at the line of weakness and withdraw the restraining sheath from over the stent device;

characterised in that:

the pull member and the line of weakness are located on opposing sides of the restraining sheath.

In the context of a restraining sheath mounted over a stent device, the meaning of opposing sides is easy to understand. Taking a cross-section of the restraining sheath, one half of that cross-section can be envisaged, which is ninety degrees either side of the pull member. The line of weakness will be located in the opposing half. Preferably, the cross-section could be split into quarters with one of the quarters circumferentially centred on the pull member and in this case, the line of weakness is located in an opposing quarter. Yet more preferably, the line of weakness and the pull member are located substantially diametrically opposite one another.

The opposing configuration allows just one pull member to be provided and still the sheath can be satisfactorily split and the restraining sheath withdrawn in its entirety so it does not remain between a wall of a bodily lumen and an outer major surface of the stent device. A reduced profile configuration at the stent device can thus be provided.

The line of weakness can be provided in a number of forms. It could be a line of perforations, a reduced material thickness line, a join between opposing sides of the restraining sheath, etc. The line of weakness can be axially straight, zigzag, sinusoidal, etc. If perforations are used, the perforations may be of any appropriate density and length and may not necessarily extend all the way through the thickness of the restraining sheath, but may instead be sufficiently deep to provide the necessary weakness. Important is that the line of weakness splits open when the pull tab is pulled during normal use of the delivery device.

The pull member has an inner part extending inside of the restraining sheath, an outer part extending outside of the restraining sheath and a wrap around portion therebetween for wrapping around an axial end of the restraining sheath for radially capturing the restraining sheath between the inner and outer parts.

Capture of the restraining sheath in this manner offers a secure way to split and collect the split restraining sheath as it is withdrawn from around the stent device.

In one embodiment, the pull member is attached to the delivery device and fixed relative to the restraining sheath at one end and an opposing end provides a pull end to be pulled in order to effect splitting and withdrawing of the restraining sheath. The pull member wraps around an axial end of the restraining sheath between the opposing ends with the inner part extending inside thereof and the outer part extending outside thereof.

Preferably, the stent device is supported on an inner member, which extends proximally from the stent device. The fixed end of the pull member may be attached to the inner member so that the pull member extends therefrom inside of the restraining sheath, wraps around an axial, preferably distal, end of the restraining sheath and returns proximally on the outside of the restraining sheath to provide the pull end.

Preferably, the restraining sheath is attached to the inner member at a position proximal of where the fixed end of the pull member is attached.

In one preferred embodiment, at least a portion of the pull member is a polymer thread. Such a thread will offer an appropriate amount of flexibility and also allows a reduced profile construction. Preferably, the polymer thread is a polyamide thread. The thread is to have a tear strength sufficient to remain intact while the restraining sheath splits at the line of weakness.

Preferably, the pull member comprises a stiffer portion attached to the polymer thread portion at a position proximal of the stent device. For example, the proximal portion could be made of metal. This ensures that the pull member has sufficient strength to perform its activation function and also sufficient flexibility where it is needed.

In another embodiment, the pull member forms a hook at one end and an opposing end provides a pull end to be pulled in order to effect splitting and withdrawing of the restraining sheath. The hook is for radially capturing an inside and an outside of the restraining sheath between inner and outer parts thereof. A wrap around portion of the hook is for engaging the axial end of the restraining sheath.

Preferably, the hook is to be moved axially before it captures an axial end of the restraining sheath. In one preferred embodiment, the delivery device comprises a storage member adjacent an axial end of the restraining sheath, which includes a recess so that the hook is stored in a reduced profile configuration for delivery. The hook is axially movable out of the recess by pulling on the pull member, whereupon it takes on a radially increased configuration for capturing the restraining sheath. The storage of the hook provides a guard against the hook damaging tissue during feeding of the stent device to the treatment site. Preferably, the pull member comprises a shape memory material, such as Nitinol, configured to expand the hook from the reduced profile configuration. Other ways of biasing the hook to the expanded position could, however, be used as would be clear to one skilled in the art, such as structural residency of the pull member material.

Preferably, the delivery device comprises a distal tip member. Preferably, the distal tip member provides the storage member and thus includes the recess. Preferably, the distal tip member is attached to an inner member upon which the stent device is mounted and supported.

In the hook embodiment, at least a portion of the pull member axially extending between (radially) the restraining sheath and the introducer sheath is flattened, thereby allowing a small profile delivery device. The pull member is stiff enough to ensure the hook maintains its hook form during withdrawal and splitting of the restraining sheath. In one preferred embodiment, the pull member is made of metal.

It is preferred that the restraining sheath be formed of an axially drawn polymer material. Preferably, the sheath is cold drawn. Even more preferably, the material is poly(ethylene terephthalate) (PET). It has been found that such materials are particularly suitable for splitting and being withdrawn according to the mechanisms of the preferred embodiments of the present invention.

Also preferred is that there be a strip of protective material located radially between the line of weakness of the restraining sheath and the stent device. This allows the line of weakness to be formed by, for example, laser and the stent device to be protected from damage occurring as a result of the formation process.

The stent device is preferably formed from a seamless tube into a framework for supporting a bodily lumen. The framework may or may not be covered, for example, with ePTFE.

The stent device is preferably of the self-expanding variety and made of a shape memory material, such as Nitinol. The framework may be made up of a number of axially spaced circumferential rings centred on the longitudinal axis of the stent device. Each of the rings may be joined to one another by several connecting struts. The rings may be formed of zig-zagging struts extending around the longitudinal axis of the stent device.

In the following, presently preferred embodiments of the invention are disclosed with reference to the drawings.

BRIEF DESCRIPTION OF THE FIGURES

FIG. 1 shows a delivery device of a first embodiment of the present invention, wherein an open loop of thread is used to capture a restraining sheath to affect splitting and withdrawal of the restraining sheath from around the stent device.

FIG. 2 shows the delivery device of FIG. 1 with the restraining sheath partially withdrawn and part of the stent device expanded.

FIG. 3 shows a delivery of a second embodiment of the present invention, wherein a pull member with a hook at a distal end is used to capture a restraining sheath to affect splitting and withdrawal of the restraining sheath from around the stent device.

FIG. 4 shows the delivery device of FIG. 3 with the restraining sheath partially withdrawn from around the stent device and a part of the stent device having been expanded.

DETAILED DESCRIPTION OF PREFERRED EMBODIMENTS OF THE INVENTION

Figure 5:
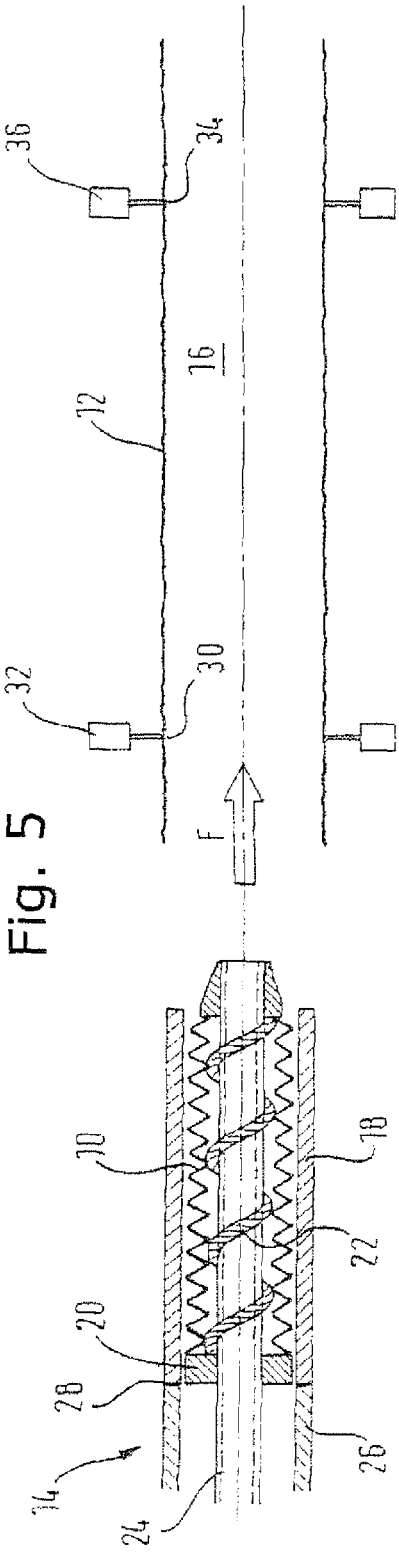
FIG. 5 discloses a longitudinal axial section through a device for loading a stent into a delivery sheath.

Referring to FIG. 1, a delivery device 1 is shown. The delivery device has a stent device 2 crimped onto an inner, tubular member 3. A restraining sheath 4 is mounted coaxially over the stent device 2 and serves to maintain the stent device 2 in the reduced profile, crimped, delivery configuration. A push member 10 is provided proximal of the stent device 2 to hold the axial position of the stent device 2 on the inner member 3 as the restraining sheath 4 is withdrawn over the stent device 2. The restraining sheath 4, the stent device 2 and a distal end region of the inner member 3 extend distally from a tubular introducer member 13.

The stent device 2 is of the self expanding variety and as such is made of a shape memory material. In the preferred embodiment, the shape memory material is Nitinol. The stent device 2 will strain against the restraining sheath 4 as it is biased to revert to its expanded configuration when it is above its phase transition temperature. The stent device 2 is made from a single tube of Nitinol and formed into a desired framework by laser cutting. The stent device 2 is formed into a number of axially spaced rings of zigzagging struts centred on a longitudinal axis of the stent device 2. Each ring is joined to another by several connector struts. The stent device 2 may be of any length including lengths of up to 300 m, perhaps between 200 mm and 300 mm.

The restraining sheath 4 is, in the preferred embodiment, formed of cold drawn PET. This material has a desirable capability to crumple as the sheath 4 is withdrawn, thereby easing the withdrawal.

A mechanism is provided to affect release of the stent device 2. This mechanism includes a pull member 5 and a line of weakness 6.

The pull member 5 includes an inner part 7 extending axially along an inside of the restraining sheath 4 and radially between the restraining sheath 4 and the stent device 2. The pull member 5 further includes an outer part 8 extending axially along an outside of the restraining sheath 4. The inner part 7 and the outer part 8 are connected by a wrap around portion 9 of the pull member 5 so that the restraining sheath is captured between the inner part 7 and the outer part 8. The wrap around portion 9 wraps around a distal end of the restraining sheath 4.

The inner part 7 is attached to the inner member 3 at a point proximal of the stent device 2 and the proximal push member 10. Glue can be used to affect the attachment. The outer part 8 extends proximally beyond the stent device 2 and the push member 10 to provide a pull end of the pull member 5, at a proximal end of the delivery device, which is usually provided with a handle. The pull end of the pull member 5 is to be pulled upon in order to exert a proximal force on the restraining sheath 4.

The pull member 5 includes a polymer thread portion 11 and a proximal stiffer portion 12. The polymer thread portion is, in the preferred embodiment a nylon thread, which is sufficiently flexible to extend inside the restraining sheath 4, wrap around a distal end of the restraining sheath 4 and return outside the restraining sheath 4. The stiffer member 12 is made of metal in order to provide a sufficiently strong material to transfer the necessary force for retracting the restraining sheath 4. The polymer thread portion 11 and the stiffer portion 12 are connected by a connection member 14. The connection member 14 is, in the preferred embodiment, a shrink tube shrunk onto the stiffer portion 12 with the polymer thread 11 clamped therebetween. The connection between the polymer thread portion 11 and the stiffer portion 12 occurs proximally of the restraining sheath 4, the stent device 2 and push member 10. The stiffer portion 12 of the pull member 5 continues to extend proximally, perhaps back to a handle if one forms part of the delivery device, to provide the pull end thereof. The pull end is to be pulled upon for actuating release of the stent device 2 from the restraining sheath 4.

The restraining sheath 4 is attached to the inner member 3 at a position proximal of where the inner part 7 of the polymer thread 11 is attached to the inner member 3. The outer part 8 of the polymer thread 11 is fed radially over the restraining sheath 4 and extends proximally beyond where the restraining sheath 4 is attached to the inner member 3. In this way, the pull member 5 forms an open loop extending around the restraining sheath 4 and extending proximally beyond the restraining sheath 4 without having to pass through the restraining sheath 4.

A distal tip member 15 of the delivery device 1 is attached to a distal end of the inner member 3. The distal tip member 15 is bulbous as compared to the inner member 3 and is tapered at its distal end. This configuration eases passage of the delivery device 1 through the vasculature of the body being treated.

The line of weakness 6 is, in the preferred embodiment, a straight line of axially extending perforations formed in the restraining sheath 4 and provided along the full length of the stent device 2 and to the distal end of the restraining sheath 4. The line of weakness 6 is disposed diametrically opposite the inner and outer parts 7, 8 of the pull member 5.

Furthermore, a protective strip 16 is positioned radially between the line of weakness 6 in the restraining sheath 4 and the stent device 2 and extending the full length of the line of weakness 6. This allows the line of weakness to be formed after the restraining sheath 4 is disposed over the stent device 2, while protecting the stent device 2 from damage as a result of the formation of the line of weakness 6.

Accordingly, the restraining sheath 4 will have diametrically opposing bumps when viewed in cross-section as a result of the protective strip 16 and the inner part 7 of the polymer thread portion 11 of the pull member. Despite this, the present embodiment allows the restraining sheath 4 to be split at the line of weakness 6 and withdrawn from being around the stent device 2 with a relatively low amount of pulling force, while at the same time providing a low profile region of the delivery device 1 where the stent device is placed, as low as 5 French (1.7 mm in diameter) with a bare stent and 6 French (2 mm in diameter) with a covered stent.

A method of releasing the stent device 2 according to the delivery device 1 of the present embodiment will now be described. The delivery device 1, with the restraining sheath 4 extending distally from the introducer member 13, is fed to a treatment site. This is usually done by passing the inner member 3 along a guide wire passing through a central lumen of the inner member 3. The guide wire serves to guide the delivery device 1 to the treatment site. Once positioned as desired, possibly with the aid of radiographic positioning, perhaps using the push member 10 as a radiographic marker, the stent device 2 is released.

To release the stent device 2, a pull end of the pull member 5 is pulled upon at a proximal end thereof, which will be outside of the body. A handle of the delivery device may include a mechanism for gripping and pulling the pull end of the pull member 5. As the pull member 5 is pulled, the proximal force on the distal end of the restraining sheath 4 by the wrap around portion 9 of the pull member 5 will cause the restraining sheath to split at the line of weakness 6. The wrap around portion 9 of the pull member 5 is able to progressively move proximally as the restraining sheath 4 splits. The stent device 2 radially expands to its original form, which is a deployed configuration, as the restraining sheath 4 splits and is withdrawn. Progressive splitting and withdrawal of the restraining sheath 4 and release of the stent device 4 to the deployed configuration is caused by continued pulling on the pulling member 5. Eventually, the restraining sheath 4 will be withdrawn past a proximal end of the stent device 2 and the stent device 2 will be fully deployed.

One can see with reference to FIG. 2, a half withdrawn restraining sheath 4. The restraining sheath 4 that has been split and withdrawn collects between the outer part 8 and the inner part 7 of the pull member 5 in a folded back and crumpled manner. The drawn material of the restraining sheath 4 is believed to aid in this desirable folding and compaction as the restraining sheath 4 is withdrawn.

With the restraining sheath 4 withdrawn and the stent device 2 deployed, the delivery device, that is the introducer member 13 and the inner member 3, can be retracted, with the inner member 3 passing through the now expanded stent device 2.

A possible method of putting together the stent device 2 and the restraining sheath 4 portion of the delivery device 1 will now be described. The stent device 2 is crimped onto the inner member 3. A nylon thread 11 is attached to the inner member 3 proximally of the stent device 2 and fed over the stent device 2. At a diametrically opposite location to the nylon thread 11, a protective strip is positioned over the stent device. A PET material is cold drawn to form an elongate tube with polymer chains of the PET aligned to a large degree. The cold drawing stretches and necks the material about the crimped stent device 2 and with the nylon thread 11 and the protective strip 16 caught between the stent device 2 and the restraining sheath 4. The restraining sheath 4 is attached to the inner member 3 at a position proximal of the attachment point of the fixed end of the nylon thread 11. The nylon thread 11 is then folded back over the outside of the restraining sheath 4 and attached to the proximal stiffer portion 12 of the pull member 5. A laser device is used, after the restraining sheath 4 is mounted coaxially over the stent device 2, to form perforations in the restraining sheath 4 along an axially straight line over where the protective strip 16 lies, thereby forming the line of weakness 6. The protective strip 16 is of such a material as to protect the stent device 2 from damage by the laser.

FIGS. 3 and 4 show a second embodiment of the present invention. The same reference numerals are used to identify like components. The second embodiment differs from the above described first embodiment in the mechanism for releasing the stent device 2 from the restraining sheath 4. It is the differences with the embodiment described above that are discussed below.

The release mechanism includes a pull member 5 having a pull end and an opposing end that is formed or formable into a hook 18, as can be seen in FIG. 4. The pull member 5 defines an inner part 7 that extends along an inside of the restraining sheath 4. The hook 18 at the end of the pull member 5 is configured to capture a distal end of the restraining sheath 4. The end of the pull member 5 is folded back onto itself to define an outer part 8 extending axially back from where the inner part 7 came from with a wrap around portion 9, where the folding took place, between the inner part 7 and the outer part 8. The distal end of the inner part 7, the wrap around portion 9 and the outer part 8, which is a proximal projection of limited extent, together define the hook 18.

The distal tip member 15 of the delivery device 1 includes a storage recess 17 for maintaining the hook 18 in a collapsed state during delivery of the delivery device 1. The collapsed state is preferably with the inner part 7 and the outer part 8 thereof pressed against one another. The collapsed state could, however, be the hook member straightened out so that the outer part 8 is not wrapped back onto the inner part 7, but instead extends distally from the inner part 7. The storage recess 17 is configured such that the radial extent of the hook 18 is reduced. The hook 18 is able to be retracted from the recess 17 upon pulling and moving of the pull member 5. Once released from the storage recess 17, the hook 18 radially expands so as to be configured to capture the restraining sheath 4 between the inner and outer parts 7,8 with the wrap around portion 19 engaging a distal end of the restraining sheath 4. The hook 18, once released, is to be moved yet further in the proximal direction before the distal end of the restraining sheath 4 is engaged and captured.

The pull end of the pull member 5 extends proximally beyond the restraining sheath 4 to be pulled on at the proximal end of the delivery device 1, perhaps at a proximal handle of the delivery device 1. The restraining sheath 4 is attached to the inner member 3 at a position axially within the introducer member 13. In order that the pull member 5 can extend inside of the restraining sheath 4 and also extend proximally therefrom, the pull member passes through the restraining sheath 4. As shown, the restraining sheath 4 is attached to the inner member 3, but with the pull member 5 encased between the restraining sheath 4 and the inner member 3 in an axially slideable manner.

The pull member 5 is, in the preferred embodiment, made of a metal material. A portion thereof at the distal end may be made of a shape memory material with an original configuration having the hook 18 formed and expanded. In this way, the hook 18 can be delivered in an opened or unfolded configuration and it will return to the hook form upon release from the storage recess 17. Otherwise, in the preferred embodiment, the pull member 5 is formed of the same metal material. The metal material ensures the hook 18 has sufficient stiffness to maintain its hook form even as the restraining sheath 4 imparts a force tending to open or unfold the hook 18 during splitting and withdrawal of the restraining sheath 4. As can be seen in the figures, the pull member 5 has a reduced profile portion 18 axially within the restraining sheath 4 and an increased profile portion 12 proximally thereof. The reduced profile portion 18 is, in the preferred embodiment, provided by flattening that portion of the pull member 5. In this way, a strong pull member 5 is provided for the majority thereof, while the portion located between the restraining sheath 4 and the stent device 2 is thinned to ensure a low profile distal end region of the delivery device 1, where the stent device 2 and restraining sheath 4 are.

As in the first embodiment, the line of weakness 6 is located diametrically opposite to the pull member 5.

The introducer member 13 and the hook 18 are arranged so that as the hook 18 passes the distal end thereof, the hook 18 is unfolded or opened by the distal end wall of the introducer member 13. This ensures that introducer member 13 can maintain a reduced profile.

A method of releasing the stent device 2 from the restraining sheath 4 will now be described. The pull end of the pull member 5 is pulled proximally in order to move the distal end of the pull member 5 out of the storage recess 17 of the distal tip member 15 attached to the inner member 3. The distal end is stored in the storage recess 17 in a collapsed hook form. Once the collapsed hook 18 moves past a restraining wall of the storage recess 17, the hook 18 radially expands.

The hook 18 proper is continued to be moved proximally by pulling on the pull member 5 and the restraining sheath 4 is engaged by the wrap around portion 9 of the hook 18 and the inner and outer parts 7, 8 capture the restraining sheath 4 therebetween. With continued pulling on the pull member 5, the hook 18 tugs on the distal end of the restraining sheath 4 causing it to split at the line of weakness 6 and causing the restraining sheath 4 to be moved proximally out of the way of the stent device 2 as it radially expands into its deployed configuration.

With reference to FIG. 4, the hook 18 moves progressively proximally, causing the sheath 4 to split at the line of weakness 6. The split sheath material is gathered by the hook 18 and the stent device 2 is released into its radially expanded deployed configuration. Gathering the split material of the restraining sheath 4 with the hook 18 ensures that sheath material is not caught between the expanded stent device 2 and an inner wall of the bodily lumen.

A possible method of making the stent device 2 and the restraining sheath 4 portion of the delivery device 1 will now be briefly described. A distal tip member 15 is attached to a distal end of the inner member 3. A storage recess 17 is formed in the distal tip member 15 so as to have a radial wall for holding the hook 18 in a collapsed configuration. A distal end region of the pull member 5 is flattened. A distal end of the flattened region of the pull member 5 is folded back upon itself to provide the hook 18. The pull member 5 is fed over the stent device 2 to be inserted with the hook 18 inserted in the storage recess 17 in a collapsed configuration with the distal end more tightly folded. At a diametrically opposite location to the pull member 5, the protective strip 16 is mounted to the stent device 2. A PET material is cold drawn into a restraining sheath 4 mounted coaxially over the stent device 2 with the pull member 5 and the protective strip 16 trapped between the stent device 2 and the restraining sheath 4. The restraining sheath 4 is attached to the inner member 3 at a position proximal of the stent device 2 with the pull member 5 extending axially therethrough. A laser is used to form perforations over where the protective strip 16 lies, thereby forming the line of weakness 6.

In the above discussion, reference has been made to cold-drawn polymers as sheath material. The following disclosure gives one example as to how a stent may be loaded into a delivery sheath, which is subsequently cold-drawn.

Reference numerals in the below disclosure relate to FIGS. 5, 6 and 7 only.

Figure 6:
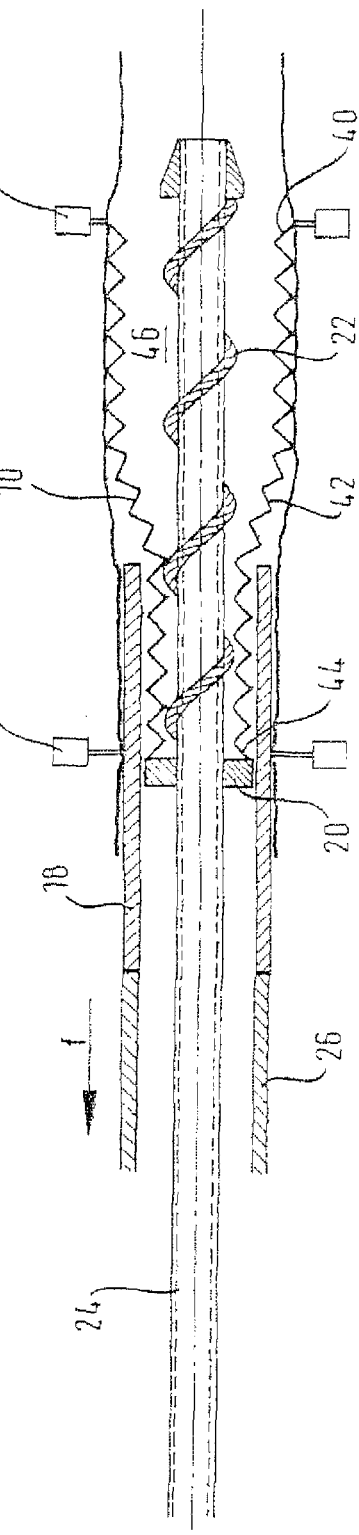
FIG. 6 disclose the device of FIG. 5, but with the stent partially loaded in the sheath.

FIG. 5 shows a crimped covered stent 10 ready for deploying from a loading sheath into a delivery sheath 12, by advancing the stent 10, in a loading tool 14 into the lumen 16 of the sheath 12, in the direction of arrow F.

The loading sheath is similar to a conventional stent deployment sheath, sized to be at least the length of the stent together with a further approximate 20% in length to provide a tolerant landing zone for the stent. It is conventionally of a braided polymer catheter material, as is generally known in the art of stent delivery systems.

The stent 10 is a radially self-expanding nickel titanium alloy stent covered in an ePTFE film. This covered stent is constrained by a loading sheath 18 in a radially compact disposition. The stent is installed in the loading sheath 18 by a "crimping" procedure known per se in which a jig (not shown) compresses the stent radially inwardly, down to its compact disposition, whereupon the stent 10 and the loading sheath 18 are moved relative to each other axially (usually by holding the sheath 18 stationary and translating the stent 10 into the lumen of the sheath 18).

In the present example, before the stent is crimped, there is inserted in its lumen a shaft 24 carrying a sequence of rings standing proud of the cylindrical surface of the shaft, or a spiral thread 22 running along the shaft. The covered stent is crimped down onto the shaft, whereupon the shaft can push the stent along its axis, supporting the stent all the way along the length of the stent, within its lumen.

The stent 10 is then "deployed" into the lumen 16 of the delivery sheath 12. For that deployment, the confining sheath 18 is pulled proximally by a pulling tube 26 contiguous with the proximal end 28 of the loading sheath 18.

During this pulling, one restrains the shaft 24 from axial movement, which prevents the stent from moving axially with the retreating loading sheath 18, so that the sheath remains in the desired location, inside the delivery sheath 12.

The delivery sheath 12 is of rather thin-walled PET tubular material. It is gripped at its proximal end 30 by an annular gripper chuck 32 and gripped at its distal end 34 by a similar annular gripping chuck 36, so that the two chucks 32 and 36 hold the opposite ends 30 and 34 of the delivery sheath 12 at a desired distance apart, while the stent is deployed into the sheath lumen 16.

This deployment process can be seen, partially completed, in FIG. 5 of the drawings, where like reference numerals identify the same components as are shown in FIG. 5. It will be appreciated that the loading sheath 18 has moved proximally, in the direction of arrow f, relative to the stent and to the stent pusher annulus 22, thereby releasing the stent 10 into the lumen 16 of the delivery sheath 12 progressively, starting at the distal end 40 of the stent, through a radially expanding portion 42 of the stent that travels the full length of the stent, from the distal end 40 to the proximal end 44 of the stent, not yet free of the confining loading sheath 18 as shown in FIG. 6. Once the full length of the stent 10 is clear of the loading sheath 18, the full radially outwardly directed stenting force from the stent 10 is carried by the delivery sheath 12, and the lumen 46 of the stent is big enough for simple proximal withdrawal from that lumen of the tubular element 24 of the loading machine.

The pull member and the protective strip can be incorporated into the delivery system and placed in the correct positions within the delivery sheath prior to deployment of the stent from the loading sheath into the delivery sheath. The stent may then be deployed against the pull member and the protective strip, to reach the desired configuration.

As explained above, the stent 10 is now radially confined within the delivery sheath 12 and can be regarded as a precursor for a "capsule" for placement at the distal end of a catheter delivery system for the stent. If desired, the loading sheath can be reused a number of times, for example ten times, before it is replaced.

Figure 7:
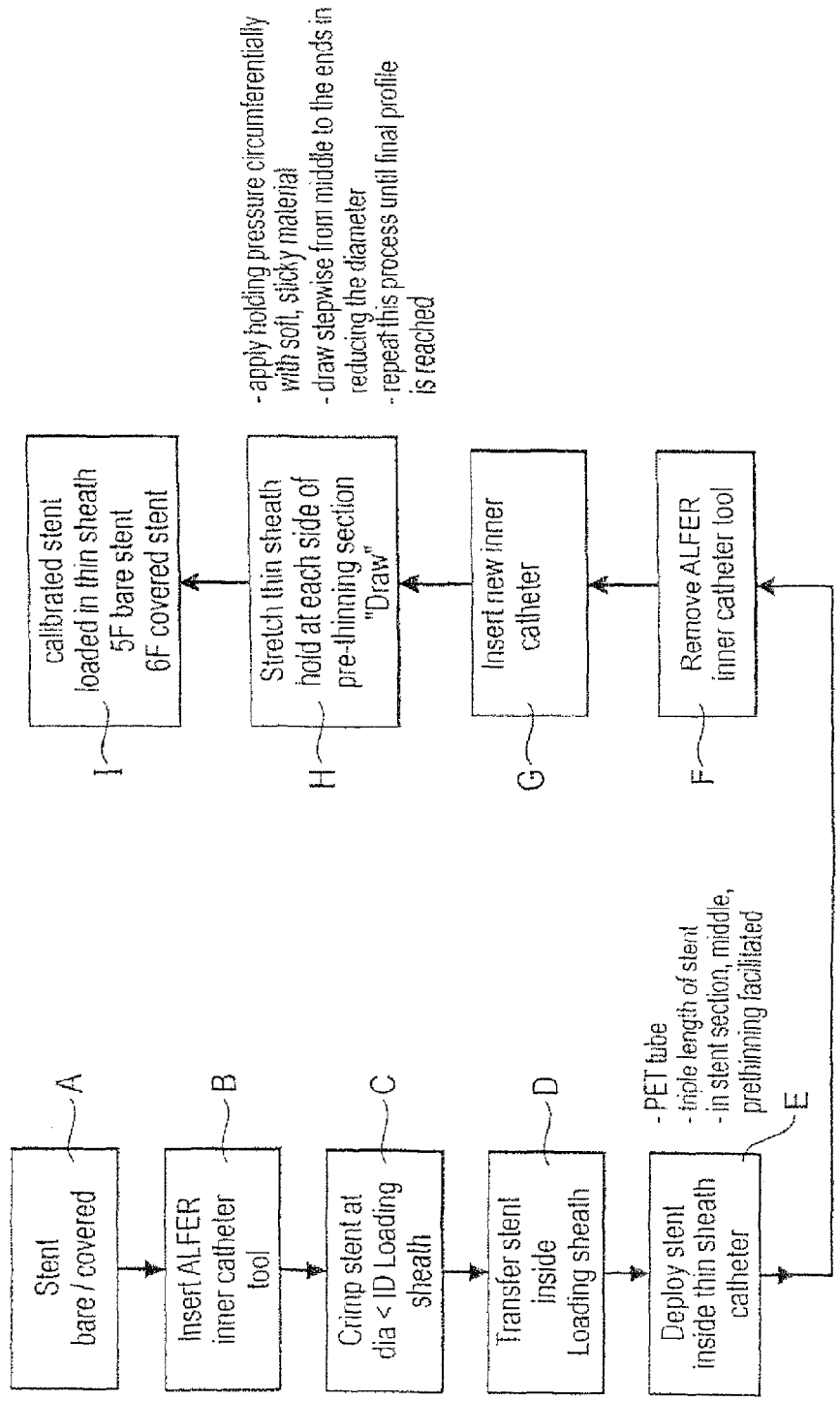
FIG. 7 discloses a flow diagram of method steps for installing a stent or stent graft within a sheath.

The process is presented in a block diagram, in drawing FIG. 7. However, FIG. 7 identifies further steps of the manufacturing process. The sequence of steps in FIG. 7 is identified by references A to I and we have the following comments on these process steps.

Step A is the step of providing the stent or stent graft of choice. A bare stent is one without any covering. A stent graft is a covered bare stent and the covering is typically of expanded polytetrafluoroethylene (ePTFE) but other covering materials are known to those skilled in the art.

Step B is the step of installing in the lumen of the chosen stent an inner catheter tool and the one preferred by the present Applicant is that described in its earlier publication WO 2004/096091 which goes by the acronym "ALFER".

Step C is the step of crimping the stent to bring the outside diameter of the chosen stent down to one that is small enough for loading the crimped stent into the chosen loading sheath 18. Next, step D, the crimped stent is translated axially into the lumen of the loading sheath 18. Then, the loading sheath carrying the stent is translated (as explained in FIGS. 5 and 6) into the lumen 16 of the delivery sheath 12 and the loading sheath 18 is withdrawn in order to deploy the stent into the delivery sheath. As noted on FIG. 7, the delivery sheath 12 is conveniently a PET tube having a length about three times that of the stent, with a pre-thinned zone in the PET tube located midway along the length of the stent in the lumen of the PET tube.

Once the stent is deployed, the inner catheter loading tool can be removed, step F, from the lumen of the deployed stent. At this point, step G, any desired component of the catheter delivery system which is to be located in the lumen of the stent can now be introduced into that lumen.

Of course, other methods of deploying stents into the lumens of e.g. body passages are known by those skilled in the art, and may with appropriate modification be employed to deploy the stent from the loading sheath to the delivery sheath in an equivalent manner.

Having prepared the stent lumen, the delivery sheath can now be cold-drawn, lengthwise, to impose substantial strain on the material of the delivery sheath. This strain will have the effect of reducing the wall thickness of the delivery sheath, and generating hoop stresses within the delivery sheath being cold-drawn, which hoop stresses will tend to compress the stent inside the lumen of the delivery sheath, and therefore marginally reduce its diameter. The FIG. 7 block diagram carries notes in relation to this step H of the process. These notes teach to use a soft sticky material to grip the delivery sheath for achieving the cold-drawing strain. Such soft, sticky materials could be silicone rubber or an adhesive composition, for example. That strain is conveniently imposed on the sheath stepwise, commencing at the midpoint of the length of the sheath and repeating the cold-drawing process, stepwise, until a final desired outside diameter profile is achieved for the sheathed stent. For example, using two gripping chucks 32 and 36, the sheath is firstly gripped at each end by the two chucks. The chucks are drawn apart to create a weak zone at the middle of the sheath. Then, the sheath is simultaneously gripped in the middle by the first gripping chuck and at one end by the second gripping chuck, then the gripping chucks are slowly drawn apart. The second gripping chuck is now moved to the new middle of the drawn sheath, and the first gripping chuck to the other end. The gripping chucks are again drawn apart. This process is repeated until a desired delivery sheath diameter is reached.

Thus, in the final step I of the process, the stent-bearing capsule is ready for combining with other components of the catheter system that is to deliver the stent to the site of stenting in the body of a patient. This is done in an entirely conventional manner, for example heat-melting the inner catheter 24 with a member of the same diameter in the proximally proximate component of the delivery system.

The above has described two preferred embodiments of the invention. Modifications to these preferred embodiments are possible and would be realised by the skilled person.

For example, one can imagine the hook 18 of the second embodiment would not necessarily need to be upwardly facing. The distal end of the pull member 5 forming the short part of the hook 18 could face inwardly towards the stent device 2. One can also envisage this inwardly facing hook 18 being positioned between the stent device 2 and the restraining sheath 4 and the remainder of the pull member 5 being outside of the restraining sheath 4. The hook 18 would thus be tucked into the restraining sheath 4 at the distal end in the delivery configuration, thereby offering a protective mechanism against the projection of the hook 18 damaging tissue. The storage recess 17 could thus be done away with.

One can also envisage a modification whereby the restraining sheath 4 is withdrawn distally rather than proximally as in the preferred embodiments. This modification has the pull member 5 extending through the lumen of the inner member 3 and out of the distal end of the delivery device 1. The pull member 5 could then be wrapped back around the distal end of the delivery device 1. The pull member 5 is then fed proximally between the stent device 2 and the restraining sheath 4 and wrapped around the proximal end of the restraining sheath 4 using a wrap around form as in the first embodiment or a hook wrap form as in the second embodiment. In this way, pulling on the pull member 5 will cause the sheath 4 to be retracted progressively from the proximal end to the distal end.

Another modification to the first embodiment that can be imagined is to attach the fixed end of the pull member 5 to the inner wall of the introducer member 13. The restraining sheath 4 could also be attached to the inner wall of the introducer member 13 at a location proximal of the attachment of the pull member 5. The pull member 5 will thus extend outside of the restraining sheath 4, wrap around the distal end of the restraining sheath and return inside of the restraining sheath 4 proximally to provide the pull end.

It can thus be seen that modifications to the presently preferred embodiments would be contemplated by the skilled person, while using the general concepts of the present invention set out in the claims and elsewhere herein.

The invention claimed is:

1. A delivery device, comprising:
a stent device, which is radially expandable from a radially reduced, delivery configuration to a radially expanded, deployment configuration;
a restraining sheath mounted coaxially over the stent device for maintaining the stent device in the delivery configuration;
the restraining sheath having a line of weakness extending axially;
a pull member to be pulled so as to split the restraining sheath at the line of weakness and withdraw the restraining sheath from over the stent device, wherein:
the pull member and the line of weakness are located on opposing sides of the restraining sheath;
the pull member has an inner part extending inside of the restraining sheath and an outer part extending outside of the restraining sheath and a wrap around portion therebetween for wrapping around an axial end of the restraining sheath for radially capturing the restraining sheath between the inner and outer parts;
the pull member forms a hook at one end and an opposing end provides a pull end to be pulled in order to affect splitting and withdrawing of the restraining sheath, wherein the hook is for radially capturing an inside and an outside of the restraining sheath between the inner and outer parts thereof;
and
the delivery device comprises a storage member adjacent an axial end of the restraining sheath, which includes a recess so that the hook is stored in a reduced profile or collapsed configuration for delivery.

2. The delivery device of claim 1, wherein the line of weakness and the pull member are located substantially diametrically opposite one another.

3. The delivery device of claim 1 wherein the line of weakness is a line of perforations.

4. The delivery device of claim 1, wherein the pull member is attached to the delivery device and fixed relative to the restraining sheath at one end and an opposing end provides a pull end to be pulled in order to affect splitting and withdrawing of the restraining sheath and wherein between the opposing ends, the pull member wraps around an axial end of the restraining sheath with the inner part extending inside of the restraining sheath and the outer part extending outside of the restraining sheath.

5. The delivery device of claim 4, wherein the stent device is supported on an inner member.

6. The delivery device of claim 5, wherein the inner member extends proximally from the stent device and the fixed end of the pull member is attached to the inner member so that the pull member extends therefrom inside of the restraining sheath, wraps around a distal end of the restraining sheath and returns proximally on the outside of the restraining sheath to provide the pull end.

7. The delivery device of claim 6, wherein the restraining sheath is attached to the inner member at a position proximal of where the fixed end of the pull member is attached.

8. The delivery device of claim 4, wherein at least a portion of the pull member is a polymer thread.

9. The delivery device of claim 8, wherein the polymer thread is a nylon thread.

10. The delivery device of claim 8, wherein the pull member comprises a stiffer metal portion attached to the polymer thread portion at a position proximal of the stent device.

11. The delivery device of claim 1, wherein the hook is movable out of the recess by pulling on the pull member and whereupon it takes on a radially increased configuration for capturing the restraining sheath.

12. The delivery device of claim 11, wherein the hook is further axially moveable upon release from the recess by pulling on the pull member to thereby engage and capture the restraining sheath with the inner and outer parts and a wrap around portion between the inner and outer parts.

13. The delivery device of claim 1, wherein a distal tip member of the delivery device provides the storage member and thus includes the recess.

14. The delivery device of claim 1, wherein at least a portion of the pull member extending axially, and radially between the restraining sheath and the introducer sheath, is flattened.

15. The delivery device of claim 1, wherein the restraining sheath is formed of an axially cold drawn polymer material.

16. The delivery device of claim 15, wherein the material of the restraining sheath is poly(ethylene terephthalate) (PET).

17. The delivery device of claim 1, further comprising a strip of protective material located radially between the line of weakness of the restraining sheath and the stent device.

* * * * *